United States Patent [19]

Fahr

[11] Patent Number: 5,376,976
[45] Date of Patent: Dec. 27, 1994

[54] ADJUSTABLE ULTRAVIOLET SHIELDING SUNGLASSES PARTICULARLY FOR CHILDREN AND INFANTS

[76] Inventor: Marybeth W. Fahr, 231 E. Richardson Ave., Langhorne, Pa. 19047

[21] Appl. No.: 84,583
[22] Filed: Jul. 1, 1993
[51] Int. Cl.5 .............................................. G02C 7/10
[52] U.S. Cl. ...................... 351/44; 351/126; 351/128; 2/452
[58] Field of Search ............... 351/41, 44, 124, 125, 351/126, 65, 158, 128; 2/10, 452, 454

[56] References Cited

U.S. PATENT DOCUMENTS

| | | | |
|---|---|---|---|
| D. 272,865 | 3/1984 | Edelmann | D2/241 |
| D. 320,608 | 10/1991 | Holtan, Jr. et al. | D16/107 |
| 901,394 | 10/1908 | Slevin | 351/126 |
| 1,141,388 | 6/1915 | George | 2/454 |
| 3,378,851 | 7/1966 | McBrayer | 2/454 |
| 4,712,254 | 12/1987 | Daigle | 2/452 |
| 4,869,586 | 9/1989 | Chung | 351/158 |
| 4,890,767 | 1/1990 | Burlison | 351/158 |
| 4,934,807 | 6/1990 | Bollé et al. | 351/62 |
| 4,955,087 | 9/1990 | Perez et al. | 2/452 |
| 4,976,530 | 12/1990 | Mackay et al. | 351/44 |

FOREIGN PATENT DOCUMENTS

| | | | |
|---|---|---|---|
| 620531 | 2/1934 | Germany | 2/452 |

Primary Examiner—William L. Sikes
Assistant Examiner—Huy Mai
Attorney, Agent, or Firm—Rhodes & Ascolillo

[57] ABSTRACT

Protective eyewear including an elongated strap member, at least a portion of the strap member being elastic, a pair of lens members, the pair of lens members being attached to the strap member adjacent opposite ends thereof, and an attachment mechanism for attaching the opposite ends of the strap member together, the attachment mechanism including: a first interlocking member disposed on a first end of the strap member, and a second interlocking member disposed on a second end of the strap member, the first and second interlocking members being releasably attachable to one another. Preferably, the length of the strap member is adjustable.

6 Claims, 1 Drawing Sheet

ADJUSTABLE ULTRAVIOLET SHIELDING SUNGLASSES PARTICULARLY FOR CHILDREN AND INFANTS

BACKGROUND

1. Field of the Invention

The present invention relates to the field of protective eyewear, particularly eyewear designed to reduce or eliminate the harmful effects of ultraviolet radiation.

Recent scientific studies have shown that protecting the eyes from harmful ultraviolet radiation is important in helping to prevent the formation of cataracts. From the earliest stages of life, eye protection is an essential part of healthy development. Most high quality sunglasses, however, are not designed for those who may require UV shielding the most, namely, infants and very young children. In order for sunglasses to be an economically feasible prospect for children, they would have to incorporate and adjustable feature to allow for the child's rapid growth rate. The present invention is directed toward addressing and overcoming these obstacles.

2. Description of the Related Art

U.S. Pat. No. 4,976,530 relates to a pair of plastic sunglasses having a removable visor snap fit to the upper edge thereof, the removable visor extending inward toward the forehead of the wearer.

U.S. Pat. No. 4,934,807 discloses a pair of sunglasses having a foam absorber strip removably attached to the frame portion over the wearer's eyes, and interchangeable lenses and temple members.

U.S. Pat. No. 4,869,586 relates to sunglasses designed to be secured to the visor of a cap and having an adjuster mechanism for regulating the angle of the sunglasses.

Finally, U.S. Des. Pats. Nos. 320,608 and 272,865 disclose various designs for sunglasses.

SUMMARY OF THE INVENTION

In one aspect, the invention features eyewear, the eyewear including: a pair of lens members; an elastic strap member interconnecting the pair of lens members; the pair of lens members being disposed at substantially the opposite ends of the elastic strap member; and a releasable interlocking mechanism for releasably interlocking the pair of lens members together.

Preferably, the releasable interlocking mechanism includes an adjustable interlocking mechanism for selectively interlocking the pair of lens members together at a plurality of positions to thereby adjust the elastic strap member to a plurality of lengths; each of the lens members is constructed of a material that substantially reduces the UV radiation passing therethrough; the adjustable interlocking mechanism includes a plurality of outstanding studs disposed on one of the ends of the strap member and a plurality of recesses for receiving the studs, the plurality of recesses being disposed on the other end of the strap member; the strap member extends across each of the lens members; the strap member additionally includes a cloth portion; the cloth portion includes at least two cloth portions, one each of the two cloth portions extending along one each of the lens members; each of the two cloth portions includes a terrycloth fabric; each of the two lens members includes a plastic material; and each of the two lens members is substantially semicircular in shape.

In another aspect, the invention features protective eyewear, the protective eyewear including: an elongated strap member; at least a portion of the strap member being elastic; a pair of lens members; the pair of lens members being attached to the strap member adjacent opposite ends thereof; and an attachment mechanism for attaching the opposite ends of the strap member together, the attachment mechanism including: a first interlocking member disposed on a first end of the strap member; and a second interlocking member disposed on a second end of the strap member; the first and second interlocking members being releasably attachable to one another.

Preferably, each of the lens members is substantially semicircular in shape and has at least one substantially straight edge, and the protective eyewear additionally includes a padding member extending across each of the substantially straight edges of the lens members; the strap member extends substantially across each of the substantially straight edges of the lens members; each of the padding members includes a portion of the strap member; each of the lens members is substantially UV blocking; the first and second interlocking members comprise a mechanism for adjusting the length of the strap member; and the first interlocking member includes a plurality of studs extending outward from the strap member, the plurality of studs being spaced along the longitudinal axis of the first end of the strap member, and the second interlocking member includes a plurality of recesses, the plurality of recesses being spaced along the longitudinal axis of the second end of the strap member.

In yet another aspect, the invention features protective eyewear for protecting the eyes of an individual from the harmful effects of UV radiation, the protective eyewear including: first and second lens members for substantially covering the eyes of the individual; an elongated strap member for extending substantially around the head of the individual; and a strap length adjustment mechanism for adjusting the length of the strap member; the first lens member being attached substantially adjacent a first end of the strap member; the second lens member being attached substantially adjacent a second end of the strap member; the first and second lens members being spaced substantially apart from one another along the length of the strap member; a portion of the strap member disposed between the first and second lens members being elastically expandable along the longitudinal axis of the strap member; and each of the first and second lens members having a substantially reduced transmission coefficient for the ultraviolet radiation spectrum.

Preferably, each of the lens members has a substantially straight edge, and the protective eyewear additionally includes an absorbent padding member extending along each of the substantially straight edges of each of the lens members; and each of the lens members is substantially semicircular in shape, the strap member extends along substantially the entire length of each of the substantially straight edges of the lens members, the strap length adjustment mechanism includes a plurality of studs extending outward from the strap member, the plurality of studs being spaced along the first end of the strap member, and a plurality of recesses spaced along the second end of the strap member, and each of the absorbent padding members includes a terrycloth fabric.

One object of the present invention is the provision of UV protective eyewear that is adjustable to fit very small infants and young children alike.

Another object of the invention is the provision of such sunglasses that can be adjusted so as to provide a range of UV protection, ranging from a maximum to a minimum.

Another object of the invention is the provision of sunglasses that are particularly suitable for infants and young children, in that they can be adjusted so as to be comfortably worn throughout the various stages of growth.

The invention will now be described by way of a particularly preferred embodiment, reference being made to the accompanying drawings, wherein:

DESCRIPTION OF THE PREFERRED EMBODIMENT

Figure 2:
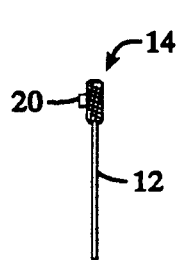
FIG. 2 is a side elevational view of the inventive sunglasses, shown in an extended planar configuration.
Figure 1:
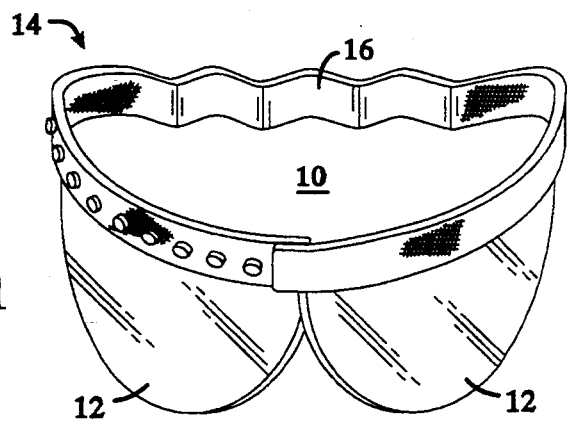
FIG. 1 is a perspective view of a pair of sunglasses constructed according to the invention, as they would be seen while being worn.
Figure 3:
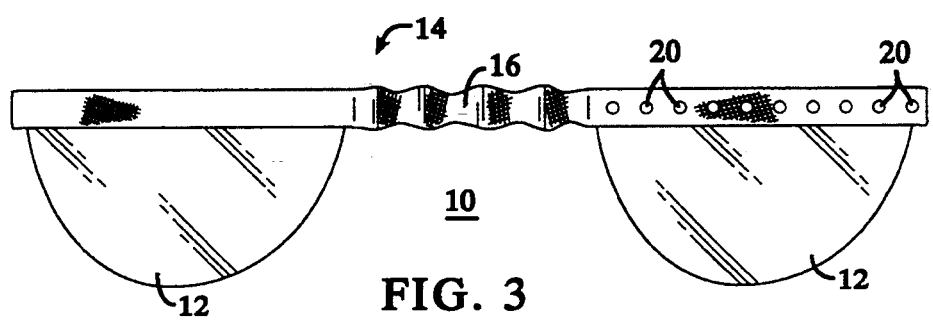
FIG. 3 is a front elevational view of the inventive sunglasses in the extended configuration.
Figure 4:
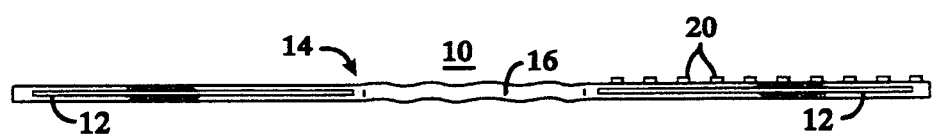
FIG. 4 is a bottom plan view of the sunglasses in the extended configuration.
Figure 5:
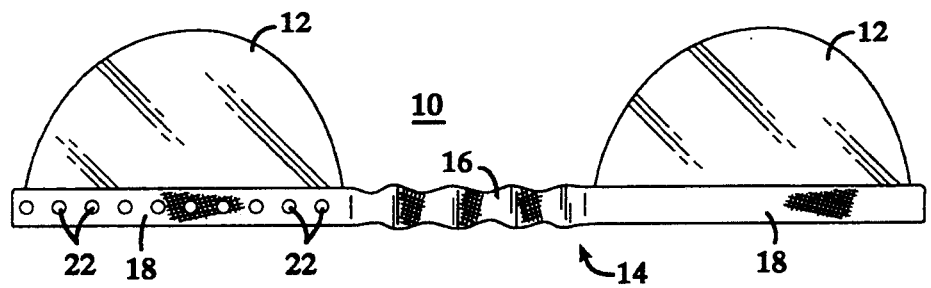
FIG. 5 is a rear elevational view of the sunglasses in the extended configuration.
Figure 6:
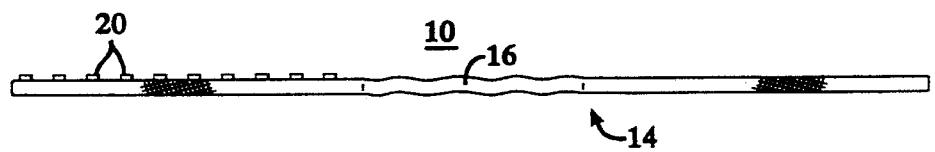
FIG. 6 is a top plan view of the sunglasses in the extended configuration.

Referring now to all of FIGS. 1-6, a protective eyewear device 10 constructed according to the present invention generally includes a pair of lenses 12 and a strap 14. As shown, the lenses 12 are generally of a substantially semicircular shape, having a substantially straight upper edge, and the strap 14, in the preferred embodiment described herein, extends substantially across the entire length of each of the straight upper edges of the lenses 12.

The lenses 12 are spaced from one another along the length of the strap 14, and the strap 14 is provided with an interior elastic portion 16 that extends over the space between the lenses 12 and interconnects the lenses 12 together. Preferably, the elastic portion 16 is constructed from an elasticized fabric well known in the art.

The lenses 12 are preferably of the type described in the art as "UV Blocking," meaning that they have a substantially reduced coefficient of transmission with respect to the ultraviolet portion of the electromagnetic radiation spectrum. Even more preferably, the lenses 12 are of the type commonly referred to as being 100% UV blocking, meaning that they transmit substantially none of the UV spectrum. Preferably, the lenses 12 are constructed from a lightweight plastic material, such UV blocking plastics now being well known in the technology of optical filters.

In order to provide for a more comfortable fit, the protective eyewear device 10 is provided with padding. Preferably, the padding extends substantially over at least a portion of each of the straight upper edges of each of the lenses 12, and even more preferably over substantially over the entire length of each of the straight upper edges of the lenses 12. Thus, the upper edge of each of the lenses 12 is provided with a pad 18 located on at least the interior portion thereof (i.e., the portion in contact with the forehead of the wearer and seen in FIG. 5). Even more preferably, the pads 18 are constructed from an absorbent material, in order to provide for the absorption of perspiration. Most preferably, the strap 14 extends over the entire length of the protective eyewear device 10, extending along the entire length of the upper straight edges of the lenses 12, and the strap 14 is most preferably constructed of an elasticized terrycloth material. In this manner, in the preferred embodiment, the pads 18 form an integral part of the strap 14 which also performs the perspiration absorption function referred to above.

The protective eyewear device 10 is equipped with an adjustable and releasable interlocking mechanism for releasably interlocking the pair of lenses 12 together. The interlocking mechanism is preferably provided in the form of a set of studs 20 (shown in FIG. 5) that are spaced evenly along one end of the strap 14 and a set of recesses (or holes) 22 that are spaced evenly along the other end of the strap 14, the recesses 22 being dimensioned to receive and retain the studs 20 in a releasable fashion. Preferably, the studs 20 and the recesses 22 are of a type similar to those often found on headgear, for example, baseball caps, that permit adjustment to a number of head sizes. Most preferably, the studs 20 are of the type that snap fit into the recesses 22.

The protective eyewear device 10 is particularly adapted to wear by either infants or very young children. As compared with presently known eyewear using ear loops, the elasticized terrycloth strap 14 reduces the likelihood that the eyewear will fall off or be disturbed. Additionally, the elasticized strap 14 may be more comfortable for the young. Still further, the adjustability of the protective eyewear 10 allows them to be worn by an infant or child throughout the various stages of growth.

While the invention has been herein described by way of a particular preferred embodiment, various substitutions of equivalents may be effected without departing from the spirit and scope of the invention as set forth in the following claims.

What is claimed is:

1. Eyewear comprising:
   (a) first and second lens members;
   (b) said lens members disposed at substantially opposite ends of an elongated strap comprising:
      (1) an elastic portion disposed between said lens members;
      (2) a releasable interlocking means for releasably interlocking said lens members in a plurality of positions, ranging from a first position of substantially complete overlap to a last position of substantially complete separation.

2. Eyewear according to claim 1 wherein means for releasably interlocking said lens members in a plurality of positions further comprises:
   (a) a plurality of outstanding studs fixedly disposed longitudinally on a first end of said elongated strap member;
   (b) a plurality of holes for receiving said studs disposed longitudinally on a second end of said elongated strap member.

3. Eyewear comprising:
   (a) first and second UV blocking lens members; and
   (b) said lens members disposed at substantially opposite ends of an elongated strap comprising:

(1) an elastic portion disposed between said lens members; and
(2) a releasable interlocking means for releasably interlocking said lens members in a plurality of positions, ranging from a first position of substantially complete overlap to a last position of substantially complete separation;
(c) said releasable interlocking means comprising:
(1) a plurality of outstanding studs disposed longitudinally on a first end of said elongated strap member; and
(2) a plurality of holes for receiving said studs disposed longitudinally on a second end of said elongated strap member.

4. Eyewear as described in claim 3, wherein said UV blocking lens member further comprises:

(a) being substantially semicircular in shape and having one substantially straight edge; and
(b) said substantially straight edge being disposed substantially parallel to a longitudinal axis of said elongated strap.

5. Eyewear as described in claim 4, wherein said lens member further comprises:

(a) an absorbent padding member fixedly attached to said substantially straight edge of said lens members;
(b) said absorbent padding men, bet disposed on a facial contact side of said lens member.

6. Eyewear as described in claim 3, wherein said elastic portion of said elongated strap further comprises an elastic, absorbent, cloth.

* * * * *